(12) United States Patent  (10) Patent No.: US 7,776,898 B2
Welsh et al.  (45) Date of Patent: Aug. 17, 2010

(54) OPIOID RECEPTOR ACTIVE COMPOUNDS

(75) Inventors: William J. Welsh, Princeton, NJ (US);
Seong Jae Yu, Pennington, NJ (US);
Anil Nair, Oro Valley, AZ (US)

(73) Assignee: The Curators of the University of Missouri, Columbia, MO (US)

( * ) Notice: Subject to any disclaimer, the term of this patent is extended or adjusted under 35 U.S.C. 154(b) by 63 days.

(21) Appl. No.: 11/857,193

(22) Filed: Sep. 18, 2007

(65) Prior Publication Data

US 2008/0070964 A1  Mar. 20, 2008

Related U.S. Application Data

(62) Division of application No. 11/337,366, filed on Jan. 23, 2006, now Pat. No. 7,294,720, which is a division of application No. 10/360,602, filed on Feb. 7, 2003, now Pat. No. 7,045,520.

(60) Provisional application No. 60/354,990, filed on Feb. 7, 2002.

(51) Int. Cl.
*A61K 31/4196* (2006.01)
*C07D 249/08* (2006.01)

(52) U.S. Cl. .................. 514/383; 548/262.2; 548/264.8

(58) Field of Classification Search .............. 548/262.2, 548/264.8; 514/383
See application file for complete search history.

(56) References Cited

U.S. PATENT DOCUMENTS

| | | | |
|---|---|---|---|
| 4,481,360 A | 11/1984 | Gall et al. | |
| 4,512,997 A | 4/1985 | Meier et al. | |
| 5,108,486 A | 4/1992 | Kondo et al. | |
| 5,310,724 A | 5/1994 | Kondo et al. | |
| 7,045,520 B2 | 5/2006 | Welsh et al. | |
| 7,294,720 B2 | 11/2007 | Welsh et al. | |
| 2006/0128776 A1 | 6/2006 | Welsh et al. | |

FOREIGN PATENT DOCUMENTS

| FR | 2269938 | 12/1975 |
|---|---|---|
| JP | 57070875 A2 | 5/1982 |
| JP | 2000-063363 | 2/2000 |
| WO | WO-99/14204 | 3/1999 |
| WO | WO-00/14066 | 3/2000 |

OTHER PUBLICATIONS

"U.S. Appl. No. 10/360,602, Response filed Oct. 22, 2004 to Restriction Requirement mailed Jun. 24, 2004", 16 pgs.
"U.S. Appl. No. 10/360,602, Restriction Requirement mailed Jun. 24, 2004", 10 pgs.
"U.S. Appl. No. 11/337,366, Restriction Requirement mailed Apr. 20, 2007", 11 pgs.
"U.S. Appl. No. 11/337,366, Response filed May 22, 2007 to Restriction Requirement mailed Apr. 20, 2007", 8 pgs.
"International Application Serial No. 03737705.8-2177, Office Action mailed Jan. 5, 2005", 11 pgs.
"International Application Serial No. 2,475,767, Office Action mailed Dec. 14, 2007", 4 pgs.
"U.S. Appl. No. 10/360,602 Amendment under 1.312 filed Dec. 19, 2005", 12 pgs.
"U.S. Appl. No. 10/360,602 Non-Final Office Action mailed Jan. 10, 2005", 9 pgs.
"U.S. Appl. No. 10/360,602 Notice of Allowance mailed Sep. 19, 2005", 9 pgs.
"U.S. Appl. No. 10/360,602 Response to Non-Final Office Action filed Jul. 11, 2005", 19 pgs.
"U.S. Appl. No. 11/337,366 Notice of Allowance mailed Jul. 2, 2007", 11 pgs.
"International Application No. PCT/US03/03746 International Preliminary Examination Report mailed Mar. 10, 2004", 19 pgs.
"International Application No. PCT/US03/03746 International Search Report mailed May 21, 2003", 9 pgs.
"International Application No. PCT/US03/03746 Response to Written Opinion filed Jan. 8, 2004", 20 pgs.
"International Application No. PCT/US03/03746 Written Opinion mailed Oct. 8, 2003", 5 pgs.
"Office Action in Mexican Patent Applictation No. 2004007719", (Mar. 28, 2007).
Abdelhamid, E. E., et al., "Selective blockage of delta opioid receptors prevents the development of morphine tolerance and dependence in mice", *Journal of Pharmacol. Exp. Ther.*, 258(1), (Jul. 1, 1991),299-303.
Bilsky, E. J., et al., "SNC 80, a selective, nonpeptidic and systemically active opioid delta agonist.", *J. Pharmacol. Exp. Ther.*, 273(1), (Apr. 1995),359-66.

(Continued)

*Primary Examiner*—Golam M Shameem
(74) *Attorney, Agent, or Firm*—Polster Lieder Woodruff & Lucchesi, L.C.

(57) ABSTRACT

The invention provides compounds of formula I:

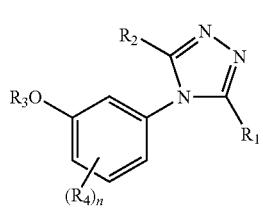

wherein $R^1$ to $R^4$ and n have any of the meanings defined in the specification and their pharmaceutically acceptable salts. The invention also provides pharmaceutical compositions comprising a compound of formula I, processes for preparing compounds of formula I, intermediates useful for preparing compounds of formula I, and therapeutic methods for treating pain and treating other conditions which involve, for example, binding opioid receptors using compounds of formula I.

6 Claims, 1 Drawing Sheet

OTHER PUBLICATIONS

Clemence, Francois, et al., "Synthese et Activite Analgesique Dans La Serie Des Triazoles-1,2,4", *European Journal of Medicinal Chemistry*, 20, Editions Scientifique Elsevier, Paris, FR,(1985),257-266.

House, R. V., et al., *Neurosci. Lett.*, 198, (1995),119.

Lange, Jerzy, et al., "4(H)-1,2,4-Triazole Derivatives with Expected Biological Activity", *Dissertations Pharmaceuticae and Pharmacologicae*, 22, (1970),217-221.

Ohsumi, Koji, et al., "Synthesis and Antitumor Activity of Cisrestricted Combretastatins: 5-Membered Heterocyclic Analogues", *Bioorganic & Medicinal Chemistry Letters*, 8, Oxford, GB,(1998),3153-3158.

Reid, L. D., et al., *Life Sciences*, 52, (1993),PL 67.

Schiller, P. W., et al., *J. Med. Chem.*, 42, (1999),3520.

Snyder, Solomon H., et al., "Historical Review: Opioid Receptors", *Trends in Pharmacological Sciences*, 24, Elsevier, Amsterdam, NL,(Apr. 2003),198-205.

Suzuki, T., et al., "Preparation of Triazoles as Arginine Vasopressin V1 Receptor Antagonists, and Pharmaceuticals Containing Them", *CAPLUS Database*, Abstract Only, Accession No. 2000:136274,(2000),2 p.

Zhang, Qiang, et al., "Discovery of Novel Triazole-Based Opioid Receptor Antagonists", *Journal of Medical Chemistry*, Supporting information,(Web Release Date: Jun. 21, 2006), S1-S37.

Zhang, Qiang, et al., "Discovery of Novel Triazole-Based Opioid Receptor Antagonists", *American Chemical Society*, (Jun. 9, 2006).

"Canadian Application Serial No. 2,475,767, Office Action Mailed Dec. 10, 2008", 2 pgs.

"Japanese Application Serial No. 2003-565474, Office Action mailed Jun. 30, 2009", 4 pgs.

OPIOID RECEPTOR ACTIVE COMPOUNDS

CROSS-REFERENCE TO RELATED APPLICATIONS

This application is a divisional of U.S. patent application Ser. No. 11/337,366, filed Jan. 23, 2006 now U.S. Pat. No. 7,294,720 which is a divisional of U.S. patent application Ser. No. 10/360,602, filed Feb. 7, 2003, now issued U.S. Pat. No. 7,045,520, which claims priority to U.S. Provisional Patent Application Ser. No. 60/354,990, filed Feb. 7, 2002, which applications and patent are herein incorporated by reference in their entirety.

BACKGROUND OF THE INVENTION

Among the three classes of opioid receptors, designated delta ($\delta$), kappa ($\kappa$), and mu ($\mu$), recent evidence suggests that u-selective opioids could be potentially useful as analgesics devoid of the numerous side effects (e.g., respiratory depression, physical dependence and gastrointestinal effects) associated with narcotics such as morphine (E. J. Bilsky et al., *J. Pharmacol. Exp. Ther.*, 273, 359 (1995)). Moreover, selective antagonists of $\delta$ receptors have been shown to modulate the development of tolerance and dependence to $\mu$ agonists such as morphine (E. E. Abdelhamid et al., *J. Pharmacol. Exp. Ther.*, 258, 299 (1991)), to modulate the behavioral effects of drugs of abuse such as cocaine (L. D. Reid et al., *Life Sci.*, 52, PL67 (1993)), and to elicit favorable immunomodulatory effects (R. V. House et al., *Neurosci. Lett.*, 198, 119 (1995)). The $\delta$-selective opioids thus represent extremely attractive candidates for a broad range of novel pharmaceutical applications including powerful yet safe analgesics, immunomodulatory agents for treating immune disorders, and new treatments for drug addiction. Opioid narcotics can be potent painkillers, but they are also addictive. The delta ($\delta$) receptors, along with the related kappa ($\kappa$) and mu ($\mu$) receptors, are found on cells located throughout the central and peripheral nervous system. The receptors normally bind with opioid peptides (e.g., enkephalins) that the body produces. By binding to the receptors, these peptides modulate endocrine, cardiovascular respiratory, gastrointestinal, and immune functions. Opioid narcotics are alkaloids, with molecular structures quite distinct from opioid peptides. However, the narcotic drugs and opioid peptides share common structural features (known as pharmacophores) that enable the drugs to bind to the opioid receptors. When they bind to these receptors, the narcotics exert various effects on the perception of pain, consciousness, motor control, mood, and autonomic function. They also induce physical dependence. However, recently published studies demonstrate that compounds, or combinations of compounds, that act in concert as selective $\mu$ agonists and $\delta$ antagonists (mixed $\mu/\delta$ agonists) exhibit the potency of opioid pain killers without their negative side effects, such as physical addiction, physical dependence, narcotic addiction, and like conditions. See P. W. Schiller et al., *J. Med. Chem.*, 1999, 42, 3520.

Despite these reports there remains a need for non-opioid compounds which possess high binding affinity and high selectivity for opioid receptors. Such compounds would be useful for treating pain as well as other opioid related conditions.

SUMMARY OF THE INVENTION

Certain triazole compounds, such as di-substituted triazole ring compounds and tri-substituted triazole ring compounds, have been discovered that exhibit high binding affinity and high selectivity for opioid receptors. Moreover, these compounds exhibit excellent bioavailability. These "non-opioid" compounds are structurally distinct from known opioid compounds such as naltrindole (NTI) and spiroindanyloxymorphone (SIOM).

Accordingly, the invention provides a compound of formula I:

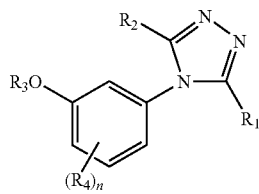

wherein:

$R_1$ is aryl, Het, $(C_{1-7})$alkyl, or $(C_{3-12})$cycloalkyl, which $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$R_2$ is H, $(C_{1-7})$alkyl, $(C_{3-12})$cycloalkyl, aryl, Het, or a group that includes one or more (1, 2, 3, or 4) basic atoms (e.g. atoms that can donate electrons or accept a proton, such as N, O, S, or P atoms);

$R_3$ is H, or $(C_{1-7})$alkyl;

each $R_4$ is independently $OR_a$, trifluoromethoxy, trifluoromethyl, halo, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-7})$alkanoyl, $(C_{2-7})$alkanoyloxy, or $(C_{3-12})$cycloalkyl;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

wherein any aryl or Het of $R^1$ or $R^2$ is optionally substituted with from 1 to 4 substituents independently selected from $OR_a$, trifluoromethoxy, trifluoromethyl, halo, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-7})$alkanoyl, $(C_{2-7})$alkanoyloxy, or $(C_{3-12})$cycloalkyl;

m is 0, 1, or 2; and n is 0, 1, 2, 3, or 4;

or a pharmaceutically acceptable salt thereof.

In another aspect, the present invention also provides:

a pharmaceutical composition comprising a compound of the invention and a pharmaceutically acceptable excipient (the composition preferably comprises a therapeutically effective amount of the compound or salt);

a method for treating a disease or condition in a mammal (e.g. a human) wherein an opioid receptor is implicated and modulation of receptor function is desired comprising administering an effective modulatory amount of a compound of the invention;

a method for treating or preventing a disease or opioid receptor related condition (e.g. pain) in a mammal comprising administering a therapeutically effective amount of a compound of the invention;

a compound of the invention for use in medical diagnosis or therapy (e.g. the treatment or prevention of opioid receptor related disease or condition such as pain, anxiety, obesity, depression, or a stress related disease);

the use of a compound of the invention to prepare a medicament useful for treating or preventing a disease or opioid receptor related condition (e.g. the treatment or prevention of opioid receptor related disease or condition such as pain, anxiety, obesity, depression, or a stress related disease);

a method of treating pain, comprising administering to a mammal in need of such treatment, an effective amount of a compound of the invention;

a method for modulating opioid receptor function in vitro or in vivo, comprising administering an effective modulatory amount of a compound of the invention; and a method for modulating opioid receptor function in vitro or in vivo, comprising contacting an opioid receptor with an effective modulatory amount of a compound of the invention.

The invention also provides novel intermediates (e.g. compounds of formula III and IV) and processes disclosed herein that are useful for preparing compounds of the invention.

DETAILED DESCRIPTION OF THE INVENTION

Figure 1A:
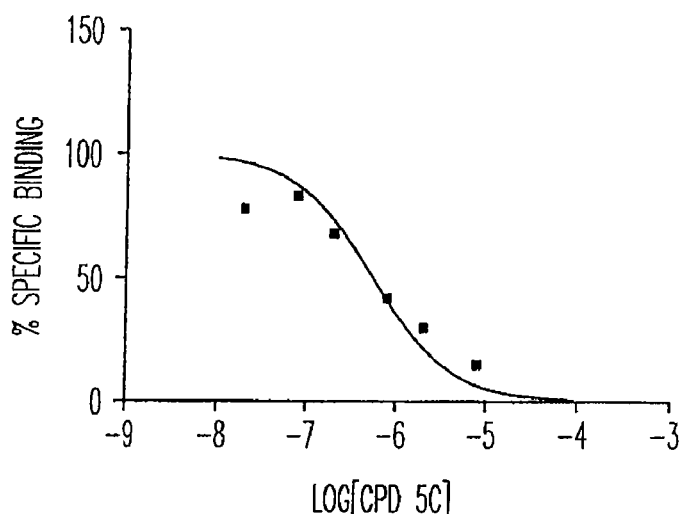
FIG. 1A-C illustrate representative dose-response curves from competitive binding assays and compounds of the present invention for the delta ($\delta$), mu ($\mu$), and kappa ($\kappa$) receptors, respectively.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to.

"Aryl" denotes a phenyl radical or an ortho-fused bicyclic carbocyclic radical having about nine to twenty ring atoms in which at least one ring is aromatic.

"Het" is a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

"Treat" or "treatment" or "treating" mean to lessen, eliminate, inhibit, improve, alter, or prevent a disease or condition, for example by administration of compound of the present invention.

"Pain" refers to, for example, a localized or generalized physical suffering associated with bodily disorder, such as a disease or an injury, and can include a basic bodily sensation induced by a noxious stimulus, received by naked nerve endings, characterized by physical discomfort such as pricking, throbbing, or aching, and typically leads to evasive action. A specific example is neuropathic pain which is a chronic condition associated with diabetes, chronic inflammation, cancer, and herpes virus infection.

"Analgesia" or "pain relief" includes, for example, inducing or providing insensitivity to pain, and preferably without loss of consciousness.

"Diseases or conditions where an opioid receptors are implicated" and "opioid receptor related disease or conditions" include, inflammation (e.g. inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, swelling occurring after injury, myocardial ischemia, allergic rhinitis, respiratory distress syndrome, endotoxin shock syndrome, atherosclerosis), pain, headache, fever, arthritis (including rheumatoid arthritis, spondyloarthopathies, gouty arthritis, osteoarthritis, systemic lupus erythematosus, and juvenile arthritis), asthma, bronchitis, menstrual cramps, tendinitis, bursitis, skin related conditions (e.g. psoriasis, eczema, burns and dermatitis), gastrointestinal conditions (e.g. inflammatory bowel disease, Crohn's disease, gastritis, irritable bowel syndrome, and ulcerative colitis), cancer (e.g. colorectal cancer), ophthalmic diseases (e.g. retinitis, retinopathies, conjunctivitis, uveitis, ocular photophobia, and acute injury to the eye tissue), pulmonary inflammation (such as that associated with viral infections and cystic fibrosis), central nervous system disorders (such as cortical dementias including Alzheimer's disease), and central nervous system damage (e.g. resulting from stroke, ischemia, or trauma). Compounds of the invention may also be useful for modifying the effects of other biologically active compounds (for example for treating narcotic addiction), and for treating diseases or conditions other than ones associated with receptors, for example, blocking, inhibiting, or promoting, metabolic pathways or enzyme function, and selectively interacting with genetic material.

In one embodiment $R_2$ is a group that includes one or more (1, 2, 3, or 4) basic atoms (e.g. atoms that can donate electrons or accept a proton, such as N, O, S, or P atoms). It is believed that a basic atom in this group mimics the basic nitrogen atom found in classical morphine-like opioids. If so, the basic atom can become protonated by acceptance of a proton, thus enhancing opioid binding affinity. Accordingly, for a compound of formula I, it may be preferred to have a group $R_2$ having a basic group that is spatially oriented so that it can mimic the basic nitrogen atom found in classical morphine-like opioids. In one embodiment, the group has a total of about 20 or less atoms including carbon atoms and one or more (1, 2, 3, or 4) basic atoms (e.g. N, O, S, or P). In another embodiment, the group has a total of about 10 or less atoms including carbon atoms and one or more (1, 2, 3, or 4) basic atoms (e.g. N, O, S, or P).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase). It is also well known in the art and, for example, as illustrated hereinbelow how to determine opioid receptor activity, for example, delta, mu, or kappa, or related receptor activity using the standard tests described herein, or using other similar tests. In particular, it is understood that compounds of formula I or II can contain chiral centers, for example, in any of the $R_1$-$R_9$ substituents.

It is also understood that compounds of the invention, such as formula I or formula II wherein, for example $R_2$ is OH or $R_3$ is hydrogen, can exist in the "enol" form or the corresponding tautomeric "keto" form, and that all such tautomers are included as compounds within the scope of the present invention.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I or formula II having any combination of the values, specific values, more specific values, and preferred values described herein.

Specifically, aryl can be phenyl, naphthyl, anthracenyl, phenanthrenyl, fluorenyl, tetrahydronaphthyl, or indanyl.

Specifically, $C_{1-7}$alkyl can be methyl, ethyl, propyl, isopropyl, butyl, iso-butyl, sec-butyl, tert-butyl, pentyl, 3-pentyl, hexyl, or heptyl; $(C_{3-12})$cycloalkyl can be cyclopropyl, cyclobutyl, cyclopentyl, cyclohexyl, cycloheptyl, cyclooctyl, or multi-cyclic substituents of the formulas

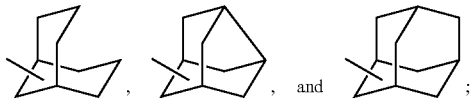

$C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; C(=O)alkyl or $(C_{2-7})$alkanoyl can be acetyl, propanoyl, butanoyl, pentanoyl, 4-methylpentanoyl, hexanoyl, or heptanoyl; aryl can be phenyl, indenyl, or naphthyl; Het can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Het is a five-(5), six-(6), or seven-(7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic Het diradical thereto.

A specific value for $R_1$ is aryl.

Another specific value for $R_1$ is aryl substituted with from 1 to 5 substituents.

Another specific value for $R_1$ is phenyl substituted with from 1 to 5 substituents.

Another specific value for $R_1$ is phenyl substituted with from 1 to 3 substituents.

Another specific value for $R_1$ is phenyl substituted with one n-butyl, iso-butyl, methyl, ethyl, or tert-butyl.

Preferred $R_1$ groups and substitutents of $R_1$, such as $R_5$, $R_6$, $R_7$, $R_8$, or $R_9$, are sterically bulky, for example, phenyl, naphthyl, pyridyl, and like aryl and Het groups, and sec-butyl, tert-butyl, cyclohexyl, adamantyl, and like alkyl or cycloalkyl groups.

Another specific value for $R_1$ is tert-butyl phenyl.

Another specific value for $R_1$ is 2-tert-butylphenyl, 3-tert-butylphenyl, or 4-tert-butylphenyl.

Another specific value for $R_1$ is 3-tert-butylphenyl, or 4-tert-butylphenyl.

Another specific value for $R_1$ is phenyl substituted with $(C_{1-7})$alkyl and $(C_{1-7})$alkoxy.

Another specific value for $R_1$ is phenyl substituted with tert-butyl and methoxy.

Another specific value for $R_1$ is Het.

Another specific value for $R_1$ is Het substituted with from 1 to 4 substituents.

Another specific value for $R_1$ is pyridyl substituted with from 1 to 4 substituents.

Another specific value for $R_1$ is pyridyl substituted with from 1 to 4 $(C_{1-7})$alkyl substituents.

Another specific value for $R_1$ is pyridyl substituted with a $(C_{1-7})$alkyl.

Another specific value for $R_1$ is pyridyl substituted with a tert-butyl.

A specific value for $R_2$ is H.

Another specific value for $R_2$ is $OR_a$.

Another specific value for $R_2$ is $SR_a$.

Another specific value for $R_2$ is $(C_{1-7})$alkyl.

Another specific value for $R_2$ is $NR_cR_d$.

Another specific value for $R_2$ is $N(CH_3)_2$.

Another specific value for $R_2$ is a piperazino, pyrrolidino, piperidino, morpholino, or thiomorpholino ring.

A specific value for $R_2$ is H, $(C_{1-7})$alkyl, $(C_{3-12})$cycloalkyl, $OR_a$, $SR_a$, $NR_cR_d$, aryl, or Het.

Another specific value for $R_2$ is a group that includes one or more N atoms.

Another specific value for $R_2$ is a group that has a total of 20 or less atoms including one or more carbon atoms and one or more basic atoms.

Another specific value for $R_2$ is a group that has a total of 20 or less atoms including one or more carbon atoms and one or more nitrogen atoms.

Another specific value for $R_2$ is a group that has a total of 20 or less atoms including one or more carbon atoms and one or two nitrogen atoms.

Another specific value for $R_2$ is a group that has a total of 10 or less atoms including one or more carbon atoms and one or more basic atoms.

Another specific value for $R_2$ is a group that has a total of 10 or less atoms including one or more carbon atoms and one or more nitrogen atoms.

Another specific value for $R_2$ is a group that has a total of 10 or less atoms including one or more carbon atoms and one or two nitrogen atoms.

Another specific value for $R_2$ is H, $(C_{1-7})$alkyl, $(C_{3-12})$cycloalkyl, $OR_a$, $SR_a$, $NR_cR_d$, aryl, Het, $R_x$—$(C_{1-7})$alkyl, $R_x$—$(C_{3-12})$cycloalkyl, $R_x$—$(C_{2-7})$alkoxy, $R_x$—$(CH_2CH_2O)_p$, or $R_x$—$(CH_2CH_2S)_p$; wherein $R_x$ is group that includes one or more basic atoms; and p is 1-7.

Another specific value for $R_2$ is H, $(C_{1-7})$alkyl, $(C_{3-12})$cycloalkyl, $OR_a$, $SR_a$, $NR_cR_d$, aryl, Het, $R_x$—$(C_{1-7})$alkyl, $R_x$—$(C_{3-12})$cycloalkyl, $R_x$—$(C_{2-7})$alkoxy, $R_x$—$(CH_2CH_2$ O)$_p$, or R$_x$—(CH$_2$CH$_2$S)$_p$; wherein R$_x$ is OR$_a$, SR$_a$, NR$_c$R$_d$, piperazino, pyrrolidino, piperidino, morpholino, or thiomorpholino; and p is 1-7.

Another specific value for R$_2$ is H, (C$_{1-7}$)alkyl, (C$_{3-12}$)cycloalkyl, OR$_a$, SR$_a$, NR$_c$R$_d$, aryl, Het, R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is NR$_c$R$_d$; and p is 1-7.

Another specific value for R$_2$ is H, (C$_{1-7}$)alkyl, (C$_{3-12}$)cycloalkyl, OR$_a$, SR$_a$, NR$_c$R$_d$, aryl, Het, R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is piperazino, pyrrolidino, piperidino, morpholino, or thiomorpholino; and p is 1-7.

Another specific value for R$_2$ is R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is group that includes one or more basic atoms; and p is 1-7.

Another specific value for R$_2$ is R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is OR$_a$, SR$_a$, NR$_c$R$_d$, piperazino, pyrrolidino, piperidino, morpholino, or thiomorpholino; and p is 1-7.

Another specific value for R$_2$ is R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is NR$_c$R$_d$; and p is 1-7.

Another specific value for R$_2$ is R$_x$—(C$_{1-7}$)alkyl, R$_x$—(C$_{3-12}$)cycloalkyl, R$_x$—(C$_{2-7}$)alkoxy, R$_x$—(CH$_2$CH$_2$O)$_p$, or R$_x$—(CH$_2$CH$_2$S)$_p$; wherein R$_x$ is piperazino, pyrrolidino, piperidino, morpholino, or thiomorpholino; and p is 1-7.

Another specific value for R$_3$ is (C$_{1-7}$)alkyl.

Another specific value for R$_3$ is methyl.

Another specific value for R$_3$ is ethyl.

Another specific value for R$_3$ is tert-butyl.

A specific value for R$_5$ is tert-butyl.

A specific value for R$_5$ is OCH$_3$ and R$_8$ is tert-butyl.

A specific value for R$_6$ is tert-butyl.

A specific value for R$_7$ is tert-butyl.

A specific compound is a compound of formula I wherein:

R$_1$ is aryl, Het, (C$_{1-7}$)alkyl, or (C$_{3-12}$)cycloalkyl, which (C$_{1-7}$)alkyl or (C$_{3-12}$)cycloalkyl are each independently optionally substituted with from 1 to 5 aryl, Het, OR$_a$, halo, NO$_2$, NR$_a$R$_b$, cyano, CONR$_a$R$_b$, CO$_2$R$_a$, SO$_m$R$_a$, S(O)$_m$NR$_a$R$_b$, or P(=O)(OR$_a$)(R$_a$);

R$_2$ is H, (C$_{1-7}$)alkyl, (C$_{3-12}$)cycloalkyl, OR$_a$, SR$_a$, NR$_c$R$_d$, aryl, or Het;

R$_3$ is H, or (C$_{1-7}$)alkyl;

R$_4$ is H, OR$_a$, trifluoromethoxy, trifluoromethyl, halo, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-7}$)alkanoyl, (C$_{2-7}$)alkanoyloxy, or (C$_{3-12}$)cycloalkyl;

R$_a$ and R$_b$ are each independently H, (C$_{1-7}$)alkyl, (C$_{3-12}$)cycloalkyl, (C$_{2-7}$)alkanoyl, (C$_{2-7}$)alkanoyloxy, or aryl, or R$_a$ and R$_b$ together with a nitrogen to which they are attached form a Het;

R$_c$ and R$_d$ are each independently H, (C$_{1-7}$)alkyl, (C$_{3-12}$)cycloalkyl, (C$_{2-7}$)alkanoyl, (C$_{2-7}$)alkanoyloxy, or aryl;

wherein any aryl or Het of R$_1$ or R$^2$ is optionally substituted with from 1 to 4 substituents independently selected from OR$_a$, trifluoromethoxy, trifluoromethyl, halo, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-7}$)alkanoyl, (C$_{2-7}$)alkanoyloxy, or (C$_{3-12}$)cycloalkyl; and m is 0, 1, or 2;

n is 1;

or a pharmaceutically acceptable salt thereof.

Another specific compound of the invention is a compound of formula II:

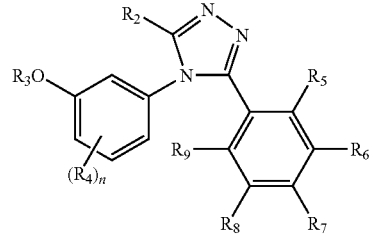

wherein:

R$_2$ is H, (C$_{1-7}$)alkyl, (C$_{3-12}$)cycloalkyl, aryl, Het, or a group that includes one or more (1, 2, 3, or 4) basic atoms (e.g. atoms that can donate electrons or accept a proton, such as N, O, S, or P atoms);

R$_3$ is H, or (C$_{1-7}$)alkyl;

each R$_4$ is independently OR$_a$, trifluoromethoxy, trifluoromethyl, halo, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-7}$)alkanoyl, (C$_{2-7}$)alkanoyloxy, or (C$_{3-12}$)cycloalkyl;

R$_5$, R$_6$, R$_7$, R$_8$, and R$_9$ are each independently H, OR$_a$, trifluoromethoxy, trifluoromethyl, halo, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-7}$)alkanoyl, (C$_{2-7}$)alkanoyloxy, or (C$_{3-12}$)cycloalkyl;

R$_a$ and R$_b$ are each independently H, (C$_{1-7}$)alkyl, (C$_{3-12}$)cycloalkyl, (C$_{2-7}$)alkanoyl, (C$_{2-7}$)alkanoyloxy, or aryl, or R$_a$ and R$_b$ together with a nitrogen to which they are attached form a Het;

wherein any aryl or Het of R$^2$ is optionally substituted with from 1 to 4 substituents independently selected from OR$_a$, trifluoromethoxy, trifluoromethyl, halo, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-7}$)alkanoyl, (C$_{2-7}$)alkanoyloxy, or (C$_{3-12}$)cycloalkyl; and m is 0, 1, or 2; and n is 0, 1, 2, 3, or 4;

or a pharmaceutically acceptable salt thereof.

A specific compound of formula II is a compound wherein R$_2$ is H, (C$_{1-7}$)alkyl, (C$_{3-12}$)cycloalkyl, OR$_a$, SR$_a$, NR$_c$R$_d$, aryl, or Het; R$_c$ and R$_d$ are each independently H, (C$_{1-7}$)alkyl, (C$_{3-12}$)cycloalkyl, (C$_{2-7}$)alkanoyl, (C$_{2-7}$)alkanoyloxy, or aryl; and n is 0 or 1.

Another specific compound is a compound wherein R$_5$, R$_6$, R$_7$, R$_8$, or R$_9$ is (C$_{1-7}$)alkyl.

Another specific compound is a compound wherein R$_5$, R$_6$, R$_7$, R$_8$, or R$_9$ is (C$_{1-7}$)alkoxy.

Another specific compound is a compound wherein R$_5$, R$_6$, R$_7$, R$_8$, or R$_9$ is OCH$_3$.

Another specific compound is a compound wherein R$_5$, R$_6$, R$_7$, R$_8$, or R$_9$ is tert-butyl.

Another specific compound is a compound wherein R$_5$, R$_6$, R$_7$, R$_8$, or R$_9$ is OH.

Another specific compound is a compound wherein R$_5$, R$_6$, R$_7$, R$_8$, and R$_9$ is H.

Another specific compound is a compound wherein R$_5$, R$_6$, R$_7$, R$_8$, or R$_9$ is halo.

Another specific compound is a compound wherein R$_5$, R$_6$, R$_7$, R$_8$, or R$_9$ is NO$_2$, (C$_{2-7}$)alkanoyloxy, (C$_{3-12}$)cycloalkyl, Het, or aryl.

Another specific compound is a compound wherein R$_5$ is OH and R$_8$ is tert-butyl.

Another specific compound is a compound wherein $R_5$ or $R_6$ is $OCH_3$, and $R_7$, $R_8$, or $R_9$ is tert-butyl.

Another specific compound is a compound wherein $R_5$ or $R_6$ is OH, and $R_7$, $R_8$, or $R_9$ is tert-butyl.

A specific compound is 1-{3-[4-(tert-butyl)phenyl]-(1,2,4-triazol-4-yl)}-3-methoxybenzene; or a pharmaceutically acceptable salt thereof.

Another specific compound is 1-{3-[4-(tert-butyl)phenyl]-(1,2,4-triazol-4-yl)}-3-phenol; or a pharmaceutically acceptable salt thereof.

Another specific compound is 1-{3-[5-(tert-butyl)-2-methoxyphenyl](1,2,4-triazol-4-yl)}-3-methoxybenzene; or a pharmaceutically acceptable salt thereof.

Another specific compound is 1-{3-[5-(tert-butyl)-2-hydroxyphenyl]-(1,2,4-triazol-4-yl)}-3-phenol; or a pharmaceutically acceptable salt thereof.

Another specific compound is 1-{3-[3-(tert-butyl)phenyl]-(1,2,4-triazol-4-yl)}-3-methoxybenzene; or a pharmaceutically acceptable salt thereof.

Another specific compound is 1-{3-[3-(tert-butyl)phenyl]-(1,2,4-triazol-4-yl)}-3-phenol; or a pharmaceutically acceptable salt thereof.

Compounds of the invention can be prepared as illustrated in the schemes below, by procedures analogous thereto, or by procedures which are known to one of ordinary skill in the art. All of the variables used in the schemes are as defined below or elsewhere herein. Scheme 1 illustrates the preparation of representative compounds of the invention, compounds 4 and 5.

Scheme 2 illustrates the preparation of an intermediate compound 6a that is useful for preparing compounds of formula I.

Scheme 2

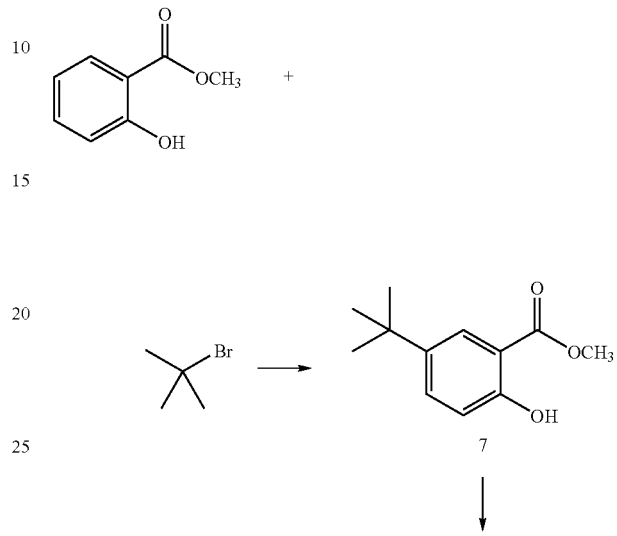

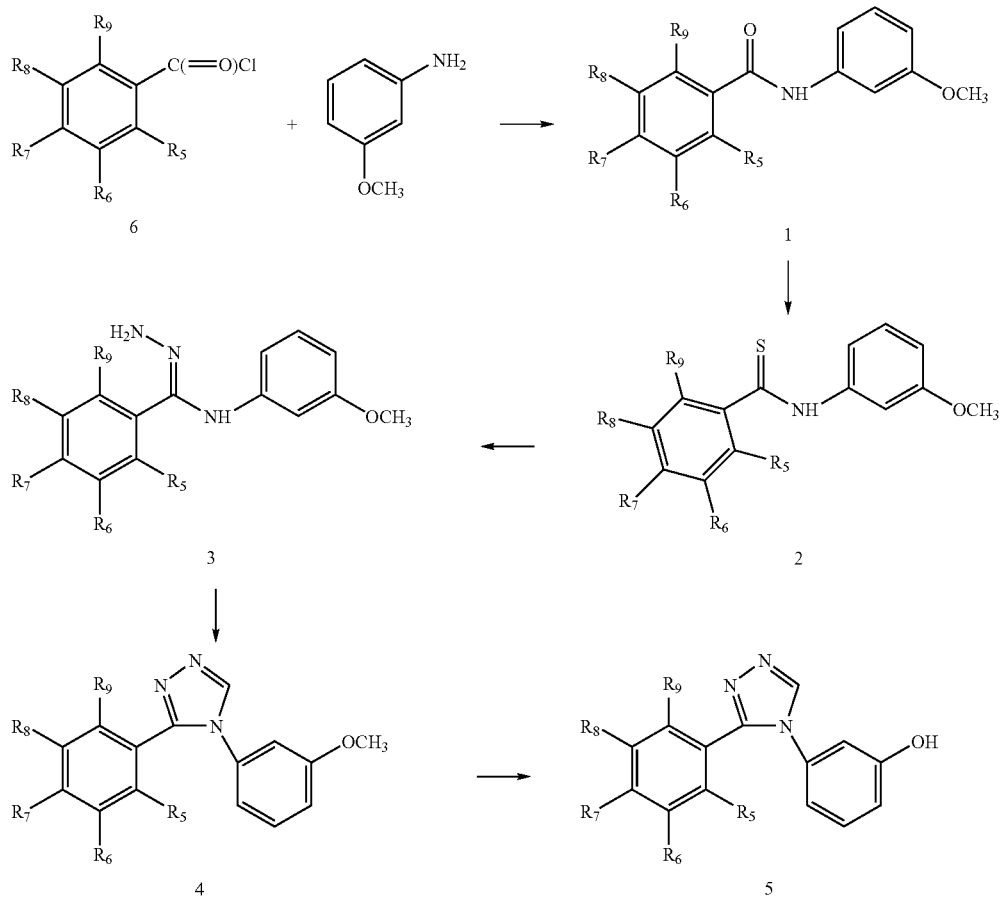

Scheme 1

-continued

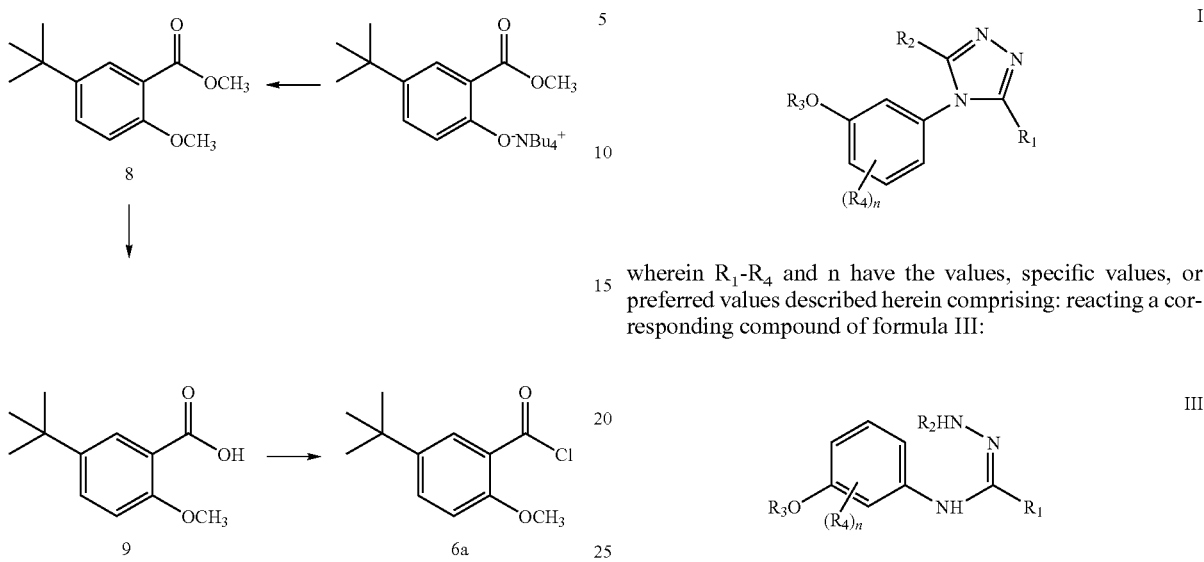

The invention also provides a method for preparing a compound of formula I:

wherein $R_1$-$R_4$ and n have the values, specific values, or preferred values described herein comprising: reacting a corresponding compound of formula III:

with a formate source to provide the compound of formula I. The reaction can be carried out under any suitable conditions. For example, the reaction can conveniently be carried out by heating the compound of formula III with pentylformate.

Scheme 3 illustrates a reaction scheme for the preparation of an intermediate compound 6b that is useful for preparing compounds of formula I.

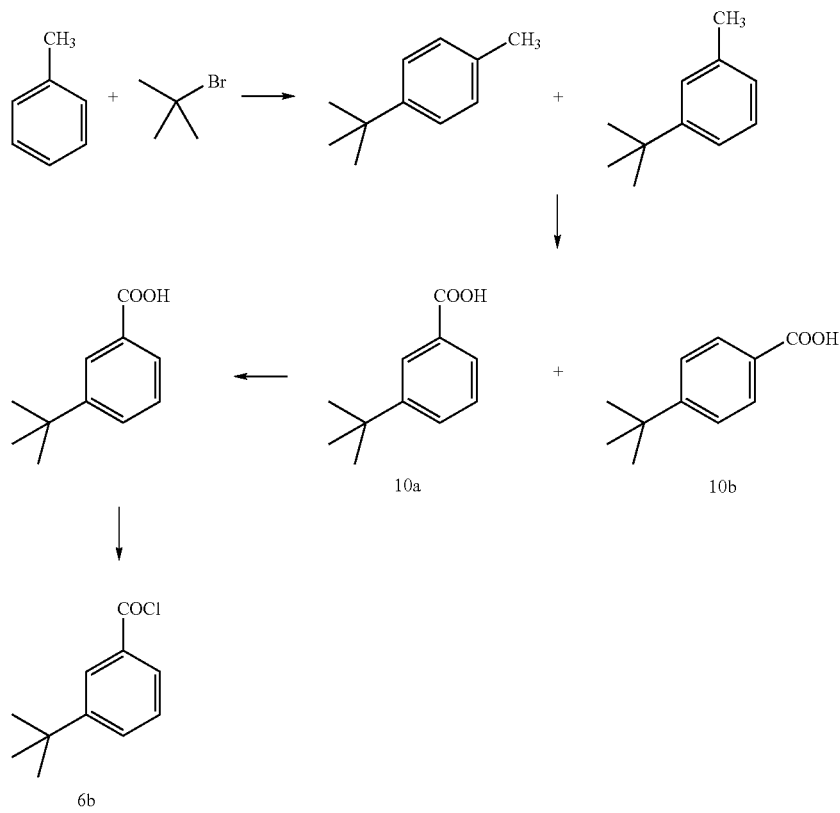

The invention also provides a method for preparing a compound of formula II:

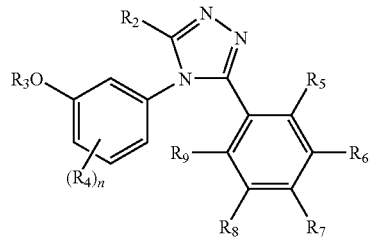

wherein $R^2$-$R^9$ have the values, specific values, or preferred values described herein comprising: reacting a corresponding compound of formula IV:

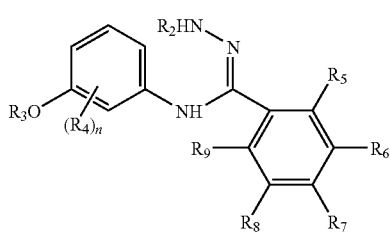

with a formate source to provide the compound of formula II. The reaction can be carried out under any suitable conditions. For example, the reaction can conveniently be carried out by heating the compound of formula III with pentylformate.

Other conditions suitable for formation of the di- or tri-substituted ring systems from a variety of intermediates as illustrated herein are well known to the art. For example, see Feiser and Feiser, "Reagents for Organic Synthesis", Vol. 1, 1967; March, J. "Advanced Organic Chemistry", John Wiley & Sons, 4$^{th}$ ed. 1992; House, H. O., "Modern Synthetic Reactions", 2$^{nd}$ ed., W. A. Benjamin, New York, 1972; and Larock, R. C., Comprehensive Organic Transformations, 2$^{nd}$ ed., 1999, Wiley-VCH Publishers, New York.

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" 2$^{nd}$ ed., 1991, New York, John Wiley & Sons, Inc. The invention also provides a method for preparing a compound of formula I comprising deprotecting a corresponding compound comprising one or more protecting groups (e.g. one or more hydroxy or amino protecting groups). For example, the invention provides a method for preparing a compound of formula I wherein $R_3$ is hydrogen comprising deprotecting a corresponding compound wherein $R_3$ is hydroxy protecting group (e.g. methyl).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metals, for example, sodium, potassium or lithium, or alkaline earth metal salts, for example calcium, of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15$^{th}$ Ed., 1975). The compounds and compositions of the present invention can be administered parenterally, for example, by intravenous, intraperitoneal or intramuscular injection, topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations typically contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1,000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1,000 mg per unit dose.

For parenteral administration or for administration as drops, as for eye treatments, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1-25, preferably from about 0.5-10, weight percent. The concentration in a semi-solid or solid composition such as a gel or a powder will be about 0.1-5 weight percent, preferably about 0.5-2.5 weight percent.

The exact regimen for administration of the compounds and compositions disclosed herein will necessarily be dependent upon the needs of the individual subject being treated, the type of treatment and, of course, the judgment of the attending practitioner.

The binding activity and binding selectivity of the compounds of the present invention are excellent predictors of the analgesic activity of compounds of the invention. The binding activity and binding selectivity can be determined using pharmacological models which are well known to the art, or using the assays described below. Exemplary results of biological testing are summarized in Table 2 below.

The non-opioid compounds of the present invention can have improved bioavailability compared with, for example, naltrindole (NTI) and spiroindanyloxymorphone (SIOM). The bioavailability of a pharmaceutical compound relates to the rate and extent at which the active ingredient reaches systemic circulation. To estimate the bioavailability of each compound, there was calculated the so-called log P that provides a measure of the molecule's hydrophobic-hydrophilic balance. Values of log P for most pharmaceuticals vary from −5 (very hydrophilic) to +5 (very hydrophobic). For example, morphine (log P of about 0.3) is considered highly hydrophilic whereas NTI (log P of about 3.3) is considered extremely hydrophobic on this Log P scale. Preferred compounds of the present invention have a log P value in the range of about 0.0 to about 2.5.

While compounds of the present invention have shown activity in the evaluations described below, these compounds may be active in opioid receptors by this or other mechanisms of action. Thus, the description below of these compounds' activity in opioid receptors is not meant to limit the present invention to a specific mechanism of action.

Six representative compounds of formula I were prepared; physical data for these compounds is provided in Table 1.

TABLE 1

Structure and Physical Data for Selected Compounds of Formula II.

| Cpd. No. | $R_{5-9}$ | $R_2$ | $R_3$ | Formula | m.p. EC | Yield (%) |
|---|---|---|---|---|---|---|
| 4a | $R_7$ = tert-butyl | H | $CH_3$ | $C_{19}H_{21}N_3O$ | 118.2-118.8 | 91.1 |
| 5a | $R_7$ = tert-butyl | H | H | $C_{18}H_{19}N_3O$ | 245-246 | 61.9 |
| 4b | $R_8$ = tert-butyl, $R_5$ = $OCH_3$ | H | $CH_3$ | $C_{20}H_{23}N_3O_2$ | 119.5-120.0 | 73.3 |
| 5b | $R_8$ = tert-butyl, $R_5$ = OH | H | H | $C_{18}H_{19}N_3O_2$ | 253.5-255.0 | 80.0 |
| 4c | $R_6$ = tert-butyl | H | $CH_3$ | $C_{19}H_{21}N_3O$ | 175.0-175.5 | 71.2 |
| 5c | $R_6$ = tert-butyl | H | H | $C_{18}H_{19}N_3O$ | 242.5-243.5 | 44.0 |
| 4d | $R_7$ = tert-butyl | $N(CH_3)_2$ | $CH_3$ | $C_{21}H_{26}N_4O$ | ! | 80% |
| 5d | $R_7$ = tert-butyl | $N(CH_3)_2$ | H | $C_{20}H_{24}N_4O$ | ! | 90% |
| 4e | $R_7$ = tert-butyl | $CH_2N(CH_3)_2$ | $CH_3$ | $C_{22}H_{28}N_4O$ | ! | 75% |

Evaluation of Biological Activity

A. In-Vitro Binding Test:

Opioid delta human receptor: This assay measures binding of [$^3$H]Naltrindole to human opiate δ receptors. CHO cells stably transfected with a plasmid encoding the human opiate δ receptor are used to prepare membranes in modified Tris-HCl pH 7.4 buffer using standard techniques. A 0.9 microgram aliquot of membrane is incubated with 0.9 nM [$^3$H]Naltrindole for 120 minutes at 25EC. Nonspecific binding is estimated in the presence of 10 micromolar (μM) naloxone. Membranes are filtered and washed 3 times and the filters are counted to determine [$^3$H]Naltrindole specifically bound. Compounds are screened at 10 μM.

Opioid kappa human receptor: This assay measures binding of [$^3$H]Diprenorphine (DPN) to human opiate κ receptors. CHO cells stably transfected with a plasmid encoding the human opiate κ receptor are used to prepare membranes in modified Tris-HCl pH 7.4 buffer using standard techniques. A 30 micrograms (μg) aliquot of membrane is incubated with 0.6 nM [$^3$H]DPN for 60 minutes at 25EC. Nonspecific binding is estimated in the presence of 10 μM naloxone. Membranes are filtered and washed 3 times and the filters are counted to determine [$^3$H]DPN specifically bound. Compounds are screened at 10 μM.

Opioid mu human receptor: This assay measures binding of the [$^3$H]Diprenorphine (DPN) to human opiate μ receptors. CHO-K1 cells stably transfected with a plasmid encoding the human opiate μ receptor are used to prepare membranes in modified Tris-HCl pH 7.4 buffer using standard techniques. An 11 μg aliquot of membrane is incubated with 0.6 nM [$^3$H]DPN for 2.5 hours at 25EC. Nonspecific binding is estimated in the presence of 10 μM naloxone. Membranes are filtered and washed 3 times and the filters are counted to determine [$^3$H]DPN specifically bound. Compounds are screened at 10 μM.

B. In-Vitro Competitive Binding:

Competitive Binding Assays. Human embryonic kidney (HEK) 293 cells (ATCC CRL, 1573) were cultured at 37° C. in Dulbecco's modified Eagle's medium supplemented with 10% fetal bovine serum, 100 units/ml penicillin and 100 μg/ml streptomycin sulfate. HEK293 cells were transfected by electroporation with expression plasmids encoding murine δ or μ opioid receptors tagged at the amino termini with the FLAG-tag epitope or the human κ receptor. Cells stably expressing opioid receptors were selected in media containing 0.75 mg/ml G418 (Life Technologies, Gaithersburg, Md.).

Cell membrane preparations were collected from the stable transfectants described above. Opioid receptor binding assays were conducted in duplicate on membrane preparations that had been resuspended in 50 mM Tris-HCL, pH 7.5, utilizing [9-$^3$H]bremazocine (specific activity 2.6 Ci/mmol, NEN, Boston, Mass.) as radioligand and 10 μM cyclazocine to define non-specific binding. Following a one-hour incubation on ice, binding assays were terminated by filtration through Whatman GF/B filters. Filters were soaked in Ecoscint liquid scintillation solution (National Diagnostics, Manville, N.J.) and filter-bound radioactivity was measured using a Packard Tri-Carb 2100 TR liquid scintillation analyzer. Receptor binding data were analyzed by non-linear regression of saturation and competition curves using Prism 3.0 software (GraphPad Software, San Diego, Calif.). Protein concentrations were determined with the Bio-Rad protein microassay (Hercules, Calif.) using bovine serum albumin as standard.

Competitive Binding Assay Results. The binding affinities for compounds listed in Table 1 (4a-c and 5a-c) were determined by competition of [9-$^3$H]bremazocine binding to membranes prepared from stable cells expressing either the cloned μ, δ, or κ opioid receptors as described in the above sections. While all compounds exhibited binding affinity for each of the three opioid receptor subtypes (inhibition ranging from 80-20%, [20 μM]), compound 5c demonstrated the greatest inhibitory effects. Compound 5c was non-selective among the three receptor subtypes at this high concentration and competed with [9-³H]bremazocine for binding to the cloned μ, δ, or κ opioid receptors.

TABLE 2

Biological Data for Selected Di-substituted Triazole Compounds of Formula II.

| Cpd. No. | Receptor Affinity (relative to 100%) | | | Selectivity for δ Receptor | |
|---|---|---|---|---|---|
| | δ | κ | μ | (δ/κ) | (δ/μ) |
| 4a | 31 | 18 | 14 | 1.72 | 2.21 |
| 5a | 21 | 48 | 18 | 0.44 | 1.17 |
| 4b | 8 | 27 | 20 | 0.30 | 0.27 |
| 5b | −0 | 20 | 21 | ! | ! |
| 4c | 2 | 27 | 19 | 0.07 | 0.11 |
| 5c | 39 | 85 | 72 | 0.46 | 0.54 |

These results demonstrate that certain di-substituted triazole compounds of the present invention are able to mimic classical opioids, for example, in their high opioid-receptor binding affinity generally. It is also significant that minor structural variations in the substituents can provide substantial changes in the receptor affinity as well as the selectivity. Thus, if desired, the compounds of the present invention can selected based on preferred receptor affinity, receptor selectivity, pain cessation properties, or based on combinations of these and other useful properties. The substituted triazole compounds of the present invention are chemically and structurally distinct from classical opioid compounds like morphine. Moreover, compounds of the present invention are more easily synthesized than the classical opioids. The compounds of the invention can also possess improved bioavailability compared with other opioid compounds and particularly with other δ-selective opioid compounds such as naltrindole (NTI) and spiroindanyloxymorphone (SIOM).

Figure 1B:
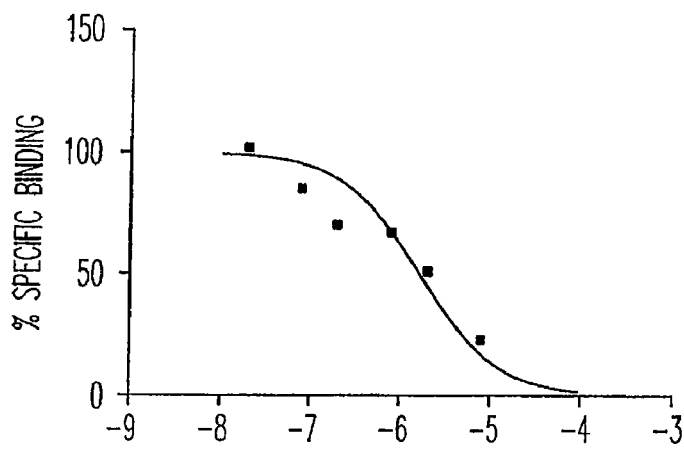
Figure 1C:
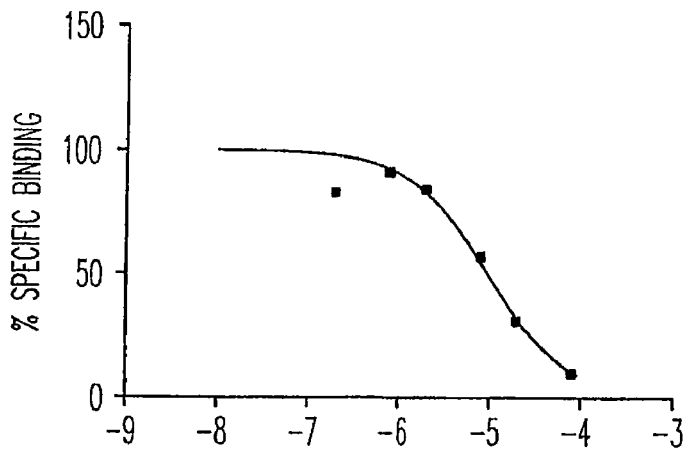

To determine the selectivity profile of compound 5c toward the cloned opioid receptors, competitive binding assays were performed in the presence of increasing concentrations of compound 5c. Referring to FIG. 1A-C, there is shown representative dose-response curves obtained from competitive binding assays of compound 5c for the delta (δ), mu (μ), and kappa (κ) receptors, respectively. Non-linear regression analysis of the curves yielded $IC_{50}$ values which were converted to inhibition constants ($K_i$) using the Cheng-Prusoff equation ($K_i = IC_{50}/(1+C/K_d)$) where C is the concentration, and $K_d$ is the apparent dissociation constant of [9-³H]bremazocine. Apparent binding constants for compound 5c at each receptor subtype are listed in Table 3. These results demonstrate that compound 5c exhibits high binding affinity (~100 nM) and moderate selectivity (1:3.3μ; 1:10 κ) for the δ opioid receptor.

TABLE 3

Average observed inhibition constant ($K_i$) values for Compounds 5c and 5d.

| Compound | Inhibition Constant, $K_i$ | | |
|---|---|---|---|
| | δ | μ | κ |
| 5c | 136 nM | 444 nM | 1390 nM |
| 5d | 300 nM | 4,000 nM | >10,000 nM |

Preliminary Test for Agonist vs. Antagonist Activity. A simple method to determine whether a compound is acting as an agonist or antagonist at a G-Protein coupled receptor is to perform the competitive binding assay in the presence of 100 mM NaCl. The presence of NaCl in the resuspension buffer will result in about a 4 fold decrease in binding affinity for an opioid receptor agonist, whereas an antagonist will show about a 1 fold increase in receptor affinity. The binding affinity curves for compound 5c in the presence of NaCl shifted left in response to about a 1 fold increase in binding affinity for all three opioid receptors. These data demonstrate that compound 5c acts as an antagonist for all of the opioid receptors subtypes tested.

C. in-vivo test: Each compound in Table 1 was evaluated for possible analgesic activity in a model of radiant heat-induced tail flick response in mice. Male or female ICR mice provided by the animal breeding center of MDS Pharma Services-Taiwan Ltd. were used. Space allocation for 10 animals was 45×23×15 cm. Mice were housed in APEC® cages (Allentown Caging, Allentown, N.J.) in a positive isolator (NuAire®, Mode: Nu-605, airflow velocity 50±5 ft/min, HEPA Filter). All animals were maintained in a controlled temperature (22EC!24EC) and humidity (60%-80%) environment with 12 hours light-dark cycles for at least one week in MDS Pharma Services—Taiwan Laboratory prior to being used. Free access to standard lab chow for mice (Fuwsow Industry Co., Limited, Taiwan) and tap water was granted. All aspects of this work including housing, experimentation and disposal of animals were performed in general accordance with the International Guiding Principles for Biomedical Research Involving Animals (CIOMS Publication No. ISBN 92 90360194, 1985). Groups of 4 male or female ICR mice weighing 22±2 gm were employed. Test substances, dissolved in a vehicle of 2% TWEEN 80/0.9% NaCl, were administrated intraperitoneally. The control group received vehicle alone. At pretreatment (0 min.) a focused beam of radiant heat was applied to the middle dorsal surface of the tail to elicit a "tail flick" response within about 6-7.5 seconds in pre-treated animals. Representative compounds of the present invention that were tested showed activity with increased response time in the "tail flick" assay compared to the response for untreated animals. No acute toxic effects were observed.

The invention will now be illustrated by the following non-limiting Examples.

General. Chemistry. All commercial reagents and solvents were used without further purification. NMR spectra were recorded on either GE QE-300 or Bruker AMX-300 spectrometers equipped with a 5.0 mm multinuclear probe. Chemical shifts are in parts per million (ppm). Using the Bruker AMX-300 spectrometer, the proton and APT (Carbon-13) NMR spectra were acquired at 30EC with sample spinning at 20 Hz. The HMQC and HMBC spectra were acquired without spinning the sample. Linear Prediction and T1 noise reduction processing were applied to the F1 dimensions of the HMQC and HMBC spectra. Mass spectra were determined using a Finnigan MAT Triple Stage (Quadrupole 7000 Mass Spectrometer (MS) equipped with and an electrospray ionization (ESI) source, and the sample was introduced into the ionization source using a Harvard Apparatus 22 Syringe Pump. Organic layers obtained after extraction of aqueous solutions were dried over anhydrous magnesium sulfate ($MgSO_4$) and filtered before evaporation in vacuo. Purity was determined by HPLC system using a Shimadzu LC-10 chromatography system equipped with LC-10AT pumps, SIL-10A XL auto injector, SCL-10A system controller, SPD-10A UV-VIS detector and Phenomenex Prodigy C 18 5 micrometer (μm) particle size column, dimensions 4.6×

EXAMPLES

Example 1

1-{3-[4-(tert-Butyl)phenyl]-(1,2,4-triazol-4-yl)}-3-methoxybenzene (4a) (Compound 4, Scheme 1, wherein $R_7$ is tert-butyl and $R_9$, $R_8$, $R_6$, and $R_5$ are hydrogen). To 1.86 g (0.006 M) of compound 3a in a 3-neck round bottom flask was added 20 mL of n-pentylformate. The resulting solution was stirred at room temperature for 1 hour and refluxed for 3 hours. After complete reaction, the product was evaporated in excess n-pentylformate under reduced pressure. The organic residue was collected by extracting with ethylacetate and water three times. The organic layer was dried over anhydrous magnesium sulfate ($MgSO_4$) and evaporated under reduced pressure. The organic residue was purified by column chromatography (ethylacetate:hexane=1:1) and yielded the title compound 1.75 g (91.1%) HPLC: $t_R$=22.67 min. $^1$H NMR (DMSO-$d_6$, 300 MHz): δ 1.30 (s, 9H), 3.76 (s, 3H), 6.76 (t, J=2.1 Hz, 1H), 6.81-6.85 (m, 1H), 6.99-7.03 (m, 1H), 7.32-7.45 (m, 5H), 8.28 (s, 1H). $^{13}$C NMR (DMSO-$d_6$, 300 MHz): δ 31.13, 34.78, 55.56, 111.68, 115.11, 118.00, 123.51, 1215.50, 128.18, 130.68, 135.86, 153.07, 153.17, 160.58. MS (Infusion/ESI/MS): m/z 308 [M+H]$^+$.

The intermediate compound 3a was prepared as follows.

a. [4-(tert-Butyl)phenyl]-N-(3-methoxyphenyl)carboxamide (1a) (Compound 1, Scheme 1, wherein $R_7$ is tert-butyl and $R_9$, $R_8$, $R_6$, and $R_5$ are hydrogen). To a solution of 3 mL (0.016M) of m-anisidine dissolved in 40 mL of dry toluene was added 2.453 mL (1.1 eq) of triethylamine. The resulting solution was stirred for 30 minutes at room temperature and 1.801 mL (1 eq) of 4-tert-butylbenzoyl chloride was added slowly dropwise. The reaction mixture was stirred for 30 minutes at room temperature and heated to about 50-60EC for 2 hours. After complete reaction, the triethylamine hydrochloride salt was filtered out and washed with 5 mL of dry toluene twice. The organic residue was extracted using water and toluene twice, and the organic layer was collected. The organic layer was dried over anhydrous magnesium sulfate ($MgSO_4$) and evaporated under reduced pressure. After recrystallization, the final product yield was 4.06 g (89.7%). $^{13}$C NMR (CDCl$_3$, 300 MHz): δ 31.23, 35.05, 55.38, 105.83, 110.50, 112.36, 125.76, 126.97, 129.76, 132.11, 139.43, 155.49, 160.27, 165.85. MS (Infusion/ESI/MS): m/z 300 [M+H]$^+$.

b. [4-(tert-Butyl)phenyl][3-methoxyphenyl)-amino]methane-1-thione (2a) (Compound 2, Scheme 1, wherein $R_7$ is tert-butyl and $R_9$, $R_8$, $R_6$, and $R_5$ are hydrogen). To 4.0 g (0.014 M) of [4-(tert-butyl) phenyl]-N-(3-methoxyphenyl) carboxamide dissolved in 40 mL of dry toluene was added 1.25 g (0.2 eq) of phosphorous pentasulfide. The resulting solution was stirred for 30 minutes at room temperature and heated to 60EC for 4 hours. After complete reaction, the organic layer was collected by extraction with toluene and water three times. The organic layer was dried over anhydrous $MgSO_4$ and evaporated under reduced pressure. After recrystallization, the final product yielded 3.80 g (89.8%). $^1$H NMR (DMSO-$d_6$, 300 MHz): δ 1.27 (s, 9H), 3.76 (s, 3H), 6.84 (dd, J=1.8 Hz, J'=1.8 Hz, 1H), 7.32 (t, J=8.1 Hz, 1H), 7.44-7.48 (m, 3H), 7.62 (s, 1H), 7.74 (d, J=8.4 Hz, 2H), 11.60 (s, 1H). $^{13}$C NMR (DMSO-$d_6$, 300 MHz): δ 30.85, 34.49, 55.11, 109.37, 111.55, 115.88, 124.67, 127.18, 129.13, 140.27, 141.17, 153.53, 159.12, 197.29. MS (Infusion/ESI/MS): m/z 300 [M+H]$^+$.

c. N$^3$-[3-Methoxyphenyl]-p-tert-butyl-benzamidrazone (3a) (Compound 3, Scheme 1, wherein $R_7$ is tert-butyl and $R_9$, $R_8$, $R_6$, and $R_5$ are hydrogen). To 5.0 g (0.017 M) of [4-(tert-butyl) phenyl][3-methoxyphenyl)-amino]methane-1-thione dissolved in 50 mL of absolute EtOH was slowly added 5.0 mL (excess) of hydrazine. The resulting solution was stirred at room temperature for 1 hour and refluxed for 2 hours. After complete reaction, the reaction mixture was evaporated under reduced pressure and in vacuo to remove traces of excess hydrazine. The final product yielded 4.8 g (96.6%). $^1$H NMR (DMSO-$d_6$, 300 MHz): δ 1.23 (s, 9H), 3.60 (s, 3H), 6.11 (s, 1H), 6.16-6.19 (m, 1H), 6.28 (dd, J=1.8 Hz, J'=2.1 Hz, 1H), 6.99 (t, J=8.1 Hz, 1H), 7.31 (d, J=8.4 Hz, 2H), 7.45 (d, J=8.7 Hz, 2H). $^{13}$C NMR (DMSO-$d_6$, 300 MHz): δ 30.85, 34.17, 54.57, 101.40, 103.91, 108.20, 124.74, 125.65, 129.34, 133.13, 138.28, 144.63, 150.13, 159.87.

Example 2

1-{3-[4-(tert-Butyl)phenyl]-(1,2,4-triazol-4-yl)}-3-phenol (5a) (Compound 5, Scheme 1, wherein $R_7$ is tert-butyl and $R_9$, $R_8$, $R_6$, and $R_5$ are hydrogen). A solution of BBr$_3$ in 10 mL of CH$_2$Cl$_2$ was added slowly to 1.0 g of 1-{3-[4-(tert-butyl) phenyl]-(1,2,4-triazol-4-yl)}-3-methoxybenzene (4a) dissolved in 10 mL of CH$_2$Cl$_2$. The resulting solution was stirred at room temperature for 2 hours. After complete reaction, the pH of the reaction mixture was adjusted to pH=2-3 using 1 M HCl solution. The organic layer was collected by extraction with CH$_2$Cl$_2$ and water three times. The organic layer was dried over anhydrous magnesium sulfate ($MgSO_4$) and evaporated under reduced pressure. The organic residue was purified by column chromatography (ethylacetate:hexane=1:1) and yielded the title compound 0.26 g (61.9%). HPLC: $t_R$=11.93 min. $^1$H NMR (DMSO-$d_6$, 300 MHz): δ 1.25 (s, 9H), 6.61 (d, J=7.8 Hz, 1H), 7.06 (s, 1H), 7.07 (d, J=2.1 Hz, 1H), 7.23 (t, J=7.2 Hz, 1H), 7.31 (d, J=8.4 Hz, 2H), 7.42 (d, J=8.7 Hz, 2H), 8.21 (s, 1H), 10.062-10.09 (broad, 1H). $^{13}$C NMR (DMSO-$d_6$, 300 MHz): δ 31.09, 34.82, 113.46, 116.53, 117.67, 122.66, 125.72, 128.25, 130.69, 134.90, 153.39, 153.71, 159.15. MS (Infusion/ESI/MS): m/z 294 [M+H]$^+$

Example 3

1-{3-[5-(tert-Butyl)-2-methoxyphenyl](1,2,4-triazol-4-yl)}-3-methoxybenzene (4b) (Compound 4, Scheme 1, wherein $R_5$ is methoxy, $R_8$ is tert-butyl and $R_6$, $R_7$, and $R_9$ are hydrogen)

The title compound was prepared using procedures similar to those described in Example 1 and the sub-parts thereof, except replacing the 4-(tert-butyl)benzoyl chloride used in sub-part a with 5-(tert-butyl)-2-methoxybenzoyl chloride 6a (Scheme 2). Compound 4b was purified by column chromatography (ethylacetate:hexane=1:1) and yielded 1.51 g (73.3%). HPLC: $t_R$=16.84 minutes. $^1$H NMR (DMSO-$d_6$, 300 MHz): δ 1.30 (s, 9H), 3.32 (s, 3H), 3.65 (s, 3H), 6.59-6.61 (m, 1H), 6.69-6.74 (m, 2H), 6.73 (dd, J=3.0 Hz, J'=1.2 Hz, 1H), 7.25 (t, J=5.6 Hz, 1H), 7.41 (dd, J=2.7 Hz, J'=3.0 Hz, 1H), 7.61 (d, J=2.4 Hz, 1H), 8.38 (s, 1H). $^{13}$C NMR (DMSO-$d_6$, 300 MHz): δ 31.42, 34.20, 54.89, 55.36, 109.54, 110.77, 114.32, 115.62, 116.02, 128.67, 128.97, 130.06, 136.57, 143.86, 152.05, 154.72, 160.18. MS (Infusion/ESI/MS): m/z 338.2 [M+H]$^+$.

The intermediate compound 6a was prepared as follows.

a. 5-(tert-Butyl)-2-hydroxybenzoic acid methyl ester (7, Scheme 2). A solution of 10 g of methylsalicylate was added to 25 mL of PPA (2 g). The resulting solution was stirred at room temperature for 1 hr and tert-butylbromide (7.58 mL, 1 eq) was added slowly dropwise. The resulting mixture was heated at 90EC for 7 hr. After the reaction was completed, the product was purified by column chromatography using n-hexane without extraction. The product yielded 13.13 g (96.0%). $^1$H NMR (CDCl$_3$, 300 MHz): δ 1.29 (s, 9H), 3.9 (s, 3H), 6.91 (d, J=90 Hz, 1H), 7.48 (d, J=9.0 Hz, 1H), 7.82 (s, 1H), 10.62 (s, 1H).

b. 5-(tert-Butyl)-2-methoxybenzoic acid methyl ester (8, Scheme 2). To 6.0 g of 5-(tert-butyl)-2-hydroxybenzoic acid methyl ester in a round bottom flask was added tetrabutyl-ammoniumhydroxide 40% solution (7.45 g, 1 eq). The resulting solution was stirred at room temperature for 2 hr. All water was evaporated under reduced pressure and then in vacuo. To remove trace water, the salt was dried in a vacuum oven overnight and yielded 12.9 g (99%). To a solution of 12.9 g of tetra-butylammonium salt in 50 ml dry THF was slowly added methyliodide (3.61 mL, 2 eq). The resulting solution was stirred at room temperature for 2 hr. After the reaction was completed, the product was filtered out using ammonium iodide salt and washed with ethylacetate twice. The pH was adjusted to pH=2-3 using 1M HCl solution. This organic layer was collected by extraction with ethylacetate and water three times. The organic layer was dried over anhydrous magnesium sulfate (MgSO$_4$). The organic layer was evaporated and the residue was purified by column chromatography (ethylacetate:hexane=1:5) (yield: 3.8 g, 60.0%) $^1$H NMR (CDCl$_3$, 300 MHz): δ 1.30 (s, 9H), 3.86 (s, 3H), 3.90 (s, 3H), 6.90 (d, J=10.5 Hz, 1H), 7.47 (d, J=9.0 Hz, 1H), 7.82 (s, 1H).

c. 5-(tert-Butyl)-2-methoxybenzoyl chloride (6a, Scheme 2). To a solution of 3.8 g of 5-(tert-butyl)-2-methoxybenzoic acid methyl ester in MeOH (30 mL) was added 50% NaOH-water solution (1 mL). The resulting solution was stirred at room temperature for 3 hr. After the reaction was complete, the pH was adjusted to pH=2-3 using 1M HCl. The reaction mixture was collected by extraction with ethylacetate and water three times. The organic layer was dried over anhydrous magnesium sulfate (MgSO$_4$) and evaporated under reduced pressure. After recrystallization, the final product yielded 3.4 g (96%). Without further purification a solution of 3.4 g of 5-(tert-butyl)-2-methoxybenzoic acid in 20 mL CH$_2$Cl$_2$ was slowly treated with SOCl$_2$ (1.2 eq). The resulting solution was stirred at room temperature for 2 hr. The reaction mixture was evaporated under reduced pressure and dried in a vacuum oven overnight to yield 3.4 g (91.9%).

Example 4

1-{3-[5-(tert-Butyl)-2-hydroxyphenyl]-(1,2,4-triazol-4-yl)}-3-phenol (5b) (Compound 5, Scheme 1, wherein R$_5$ is hydroxy, R$_8$ is tert-butyl and R$_6$, R$_7$, and R$_9$ are hydrogen). Compound 5b was prepared from 1-{3-[5-(tert-butyl)-2-methoxyphenyl](1,2,4-triazol-4-yl)}-3-methoxybenzene (4b) using a procedure similar to that described in Example 2. Compound 5b was purified by column chromatography (ethylacetate:hexane=1:1) and yielded 0.22 g (80.0%) final product. HPLC: t$_R$=8.60 min. $^1$H NMR (DMSO-d$_6$, 300 MHz): δ 1.00 (s, 9H), 6.83-6.86 (m, 2H), 6.97-7.00 (m, 2H), 7.03-7.08 (m, 1H), 7.26 (dd, J=2.4 Hz, J'=2.4 Hz, 1H), 7.34-7.38 (m, 1H), 8.22 (s, 1H), 9.40-9.70 (broad, 1H), 11.30-11.60 (broad, 1H). $^{13}$C NMR (DMSO-d$_6$, 300 MHz): δ 30.77, 33.49, 109.15, 113.59, 116.77, 116.87, 117.39, 123.35, 128.42, 130.71, 135.50, 140.91, 151.87, 155.37, 159.06. MS (Infusion/ESI/MS): m/z 310 [M+H]$^+$ Example 5

1-{3-[3-(tert-Butyl)phenyl]-(1,2,4-triazol-4-yl)}-3-methoxybenzene (4c) (Compound 4, Scheme 1, wherein R$_6$ is tert-butyl and R$_5$, R$_7$, R$_8$, and R$_9$ are hydrogen). The title compound was prepared using procedures similar to those described in Example 1 and the sub-parts thereof, except replacing the 4-(tert-butyl)benzoyl with 3-(tert-butyl)benzoyl chloride (6b) (Scheme 3). Compound 4c was purified by column chromatography (ethylacetate:hexane=1:1) and yielded 0.89 g (71.2%) final product. HPLC: t$_R$=19.79 min. $^1$H NMR (DMSO-d$_6$, 300 MHz): δ 1.18 (s, 9H), 3.75 (s, 3H), 6.74 (t, J=2.3 Hz, 1H), 6.82-6.85 (m, 1H), 6.98-7.02 (m, 1H), 7.34-7.45 (m, 5H), 8.31 (s, 1H). $^{13}$C NMR (DMSO-d$_6$, 300 MHz): δ 31.06, 34.66, 55.60, 111.85, 115.06, 118.03, 125.79, 125.89, 126.00, 126.83, 128.39, 130.70, 135.98, 151.40, 153.52, 160.69. MS (Infusion/ESI/MS): m/z 308 [M+H]$^+$.

The intermediate compound 6b was prepared as follows.

a. 3-tert-Butyl-benzoic acid (10a, Scheme 3). To a solution of dry toluene 53.1 mL (0.5 mole) was added anhydrous AlCl$_3$ (6.667 g, 0.05 mole). The resulting solution was stirred at 5EC for 30 min while slowly treated with tert-butylchloride dropwise 5.435 mL (0.05 mole) at below 10EC. The resulting solution was stirred at below 20EC for 3 hr. After the reaction was complete, the organic layer was collected by extraction with water and toluene three times. The organic layer was dried over anhydrous magnesium sulfate (MgSO$_4$) and evaporated under reduced pressure. This yielded a 6.44 g (87.0%) mixture of 3-tert-butyltoluene and 4-tert-butyltoluene. Without further purification of 6.44 g of the mixture was added to 20.4 g (3 eq) of KMnO$_4$ solution in pyridine (96.7 mL) and water (64.5 mL). The resulting solution was stirred at room temperature for 30 min and heated to boiling, ca.100EC. After the reaction was complete, the pH was adjusted to pH=2-3 using 1M HCl solution then the product was extracted with ethylacetate and water twice. The organic layer was washed with 1M HCl solution to remove excess pyridine, then collected. The organic layer was dried over anhydrous magnesium sulfate (MgSO$_4$) and evaporated under reduced pressure. Recrystallization yielded a 7.1 g (92.2%) mixture of 3-tert-butyl benzoic acid and 4-tert-butylbenzoic acid. The 3-tert-butylbenzoic acid and 4-tert-butylbenzoic acid were separated by recrystallization from MeOH to provide compound 10a. HPLC t$_R$=26.63 min. $^1$H NMR (CDCl$_3$, 300 MHz): δ 1.36 (s, 9H), 7.41 (t, J=8.0 Hz, 1H), 7.63-7.67 (m, 1H), 7.95 (d, J=8.0 Hz, 1H), 8.17 (s, 1H).

b. Compound 6b was prepared from 3-tert-butylbenzoic acid using a procedure similar to that described in Example 3, sub-part c.

Example 6

1-{3-[3-(tert-Butyl)phenyl]-(1,2,4-triazol-4-yl)}-3-phenol (5c). Compound 5c was prepared from 1-{3-[3-(tert-butyl)phenyl]-(1,2,4-triazol-4-yl)}-3-methoxybenzene (4c) using a procedure similar to that described in Example 2. Compound 5c was purified by column chromatography (ethylacetate:hexane=1:1) and yielded 0.11 g (44.0%) final product. HPLC: t$_R$=10.64 min. $^1$H NMR (DMSO-d$_6$, 300

MHz): δ 1.12 (s, 9H), 6.69 (t, J=1.5 Hz, 1H), 6.74-6.78 (m, 1H), 6.87-6.91 (m, 1H) 7.27-7.43 (m, 5H), 8.77 (s, 1H). $^{13}$C NMR (DMSO-d$_6$, 300 MHz): δ 30.64, 34.16, 113.11, 116.21, 116.29, 125.01, 125.26, 126.13, 126.31, 128.37, 130.41, 135.50, 150.56, 152.20, 158.80. MS (Infusion/ESI/MS): m/z 294 [M+H]$^+$.

Example 7

1-{3-[4-(tert-butyl)phenyl]-5-N,N-dimethylamino-(1,2,4-triazol-4-yl)}-3-methoxylbenzene (4d)

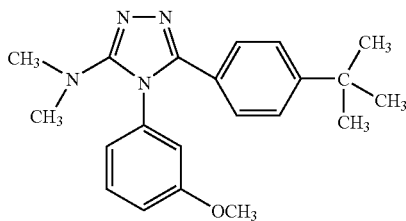

To 600 mg of Compound 3 (Scheme 1) in a three-necked round bottom flask was added 10 ml dichloromethane and 0.74 ml triethylamine. After stirring at room temperature for 10 minutes, 326 mg Viehe's reagent was added. The suspension was stirred at reflux temperature until the solid disappeared. After cooling to room temperature, the solution was diluted by dichloromethane and extracted by water. The organic layer was dried by anhydrous magnesium sulfate and concentrated by evaporation under vacuum. The crude product was purified by flash chromatography to give a colorless crystal product in 80% yield. $^1$H NMR(CDCL3, 400 MHz): 1.24 (s, 9H), 2.63 (s, 6H), 3.75 (s, 3H), 6.95 (d, J=0.9 Hz, 1H), 7.04 (s, 1H), 7.10 (d, J=0.9 Hz, 1H), 7.25 (d, J=6.7 Hz, 2H), 7.32-7.34 (m, 2H) 7.41-7.43 (m, 1H), MS(EI): 351.3 (M+H)$^+$, 336.3, 295.3, 224.3.

Example 8

1-{3-[4-(tert-butyl)phenyl]-5-N,N-dimethylamino-(1,2,4-triazol-4-yl)}-3-phenol (5d)

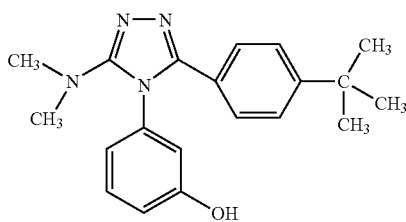

Compound 4d (17.5 mg) was dissolved in 5 ml dry dichloromethane, and cool the solution to −78° C. 0.17 ml 1M Boron tribromide solution was dropped carefully under stirring. After dropping, the solution was stirred at room temperature for 3 hours. The solution was transferred to beaker and neutralized by hydrogen chloride solution. The organic solution was extracted by water for two times and dried by anhydrous magnesium sulfate. After concentration the crude product was purified by flash chromatography to get a white solid with 90% yield. $^1$H NMR(CDCL3, 400 MHz): 1.23 (s, 9H), 2.61 (s, 6H), 6.64 (d, J=7.9 Hz, 1H), 6.99 (s, 1H), 7.10 (d, J=8.3 Hz, 1H), 7.22-7.27 (m, 5H), 10.93 (s, 1H). MS (EI): 337.4 (M+H)$^+$, 322.3, 307.3, 281.3, 266.3, 210.3.

Example 9

1-{3-[4-(tert-butyl)phenyl]-5-N,N-dimethylaminoethyl-(1,2,4-triazol-4-yl)}-3-methoxylbenzene (4e)

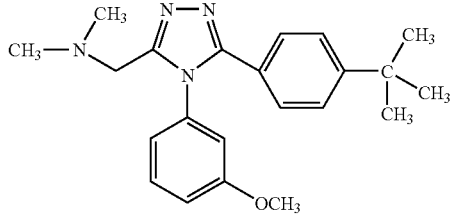

Compound 3 (Scheme 1, 123 mg, 0.4 mmol) was dissolved in 5 ml dry DMF at the room temperature. Eschenmoser's reagent 183 mg (1 mmol) was added rapidly under argon. The suspension was stirred at the 80° C. for 5 hours. After cooling to room temperature the solution was concentrated under vacuum and the residue was dissolved in acetone. The product was further purified by flash chromatography to give colorless syrup product with yield of 75%. $^1$H NMR (CDCL3, 400 MHz): 1.27 (s, 9H), 2.27 (s, 6H), 3.43 (s, 2H), 3.78 (s, 3H), 6.85 (d, J=7.9 Hz, 1H), 6.97 (s, 1H), 7.01 (D, J=8.2 Hz, 1H), 7.28-7.40 (m, 5H). MS (EI): 365.2 (M+H)$^+$, 320.2, 308.2.

Example 10

The following illustrate representative pharmaceutical dosage forms, containing a compound of the invention ('Compound X'), such as a compound of formula I or II for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |

-continued

| | |
|---|---|
| Pregelatinized starch | 120.0 |
| Magnesium stearate | 3.0 |
| | 600.0 |
| (iv) Injection 1 (1 mg/ml) | mg/ml |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to treat pain comprising administering to a mammal in need of such treatment, an effective amount of a compound of formula (I):

I wherein:

$R_1$ is aryl, Het, $(C_{1-7})$alkyl, or $(C_{3-12})$cycloalkyl, which $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$R_2$ is H, $(C_{1-7})$alkyl, $(C_{3-12})$cycloalkyl, aryl, Het, or a group that includes one or more basic atoms;

$R_3$ is H, or $(C_{1-7})$alkyl;

each $R_4$ is independently $OR_a$, trifluoromethoxy, trifluoromethyl, halo, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-7})$alkanoyl, $(C_{2-7})$alkanoyloxy, or $(C_{3-12})$cycloalkyl;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

wherein any aryl or Het of $R^1$ or $R^2$ is optionally substituted with from 1 to 4 substituents independently selected from $OR_a$, trifluoromethoxy, trifluoromethyl, halo, $NO_2$, $NR_aR_b$, cyano, $CONR_aR_b$, $CO_2R_a$, $SO_mR_a$, $S(O)_m NR_aR_b$, $P(=O)(OR_a)(R_a)$, $(C_{1-7})$alkyl, $(C_{2-7})$alkanoyl, $(C_{2-7})$alkanoyloxy, or $(C_{3-12})$cycloalkyl; and m is 0, 1, or 2;

n is 0, 1, 2, 3, or 4;

or a pharmaceutically acceptable salt thereof.

2. The method of claim 1, wherein $R^1$ comprises aryl optionally substituted with from 1 to 4 $(C_{1-7})$alkyl groups.

3. The method of claim 1, wherein $R^2$ comprises an amino group.

4. The method of claim 1, wherein $R^3$ is H.

5. The method of claim 1, wherein n=0.

6. The method of claim 1, wherein the compound of formula (I) is:

* * * * *